US009809823B2

(12) United States Patent
Maher, III et al.

(10) Patent No.: US 9,809,823 B2
(45) Date of Patent: *Nov. 7, 2017

(54) DNA APTAMERS FOR PROMOTING REMYELINATION

(71) Applicant: Mayo Foundation for Medical Education and Research, Rochester, MN (US)

(72) Inventors: Louis J. Maher, III, Rochester, MN (US); Moses Rodriguez, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,359

(22) Filed: Oct. 10, 2016

(65) Prior Publication Data

US 2017/0088839 A1 Mar. 30, 2017

Related U.S. Application Data

(63) Continuation of application No. 14/837,513, filed on Aug. 27, 2015, now Pat. No. 9,481,887, which is a continuation of application No. 14/114,392, filed as application No. PCT/US2012/035005 on Apr. 25, 2012, now Pat. No. 9,150,867.

(60) Provisional application No. 61/565,144, filed on Nov. 30, 2011, provisional application No. 61/480,179, filed on Apr. 28, 2011.

(51) Int. Cl.
| | |
|---|---|
| *C07H 21/02* | (2006.01) |
| *C07H 21/04* | (2006.01) |
| *A61K 31/70* | (2006.01) |
| *C12N 15/115* | (2010.01) |
| *C12N 5/00* | (2006.01) |

(52) U.S. Cl.
CPC ........ *C12N 15/115* (2013.01); *C12N 2310/16* (2013.01)

(58) Field of Classification Search
None
See application file for complete search history.

(56) References Cited

U.S. PATENT DOCUMENTS

| 9,481,887 | B2 | 11/2016 | Maher, III et al. | |
|---|---|---|---|---|
| 2006/0193821 | A1* | 8/2006 | Diener | C07H 21/04 424/78.37 |
| 2007/0105805 | A1* | 5/2007 | Kmiec | C12N 15/115 514/44 R |
| 2008/0233132 | A1 | 9/2008 | Miller et al. | |
| 2009/0234105 | A1 | 9/2009 | Gervay-Hague et al. | |
| 2010/0074907 | A1 | 3/2010 | Mi et al. | |
| 2012/0165401 | A1* | 6/2012 | Nakamura | C12N 15/115 514/44 R |
| 2014/0148501 | A1 | 5/2014 | Maher, III | |
| 2016/0017333 | A1 | 1/2016 | Maher, III | |

FOREIGN PATENT DOCUMENTS

| EP | 1964574 | 9/2008 |
|---|---|---|
| WO | WO 95/30004 | 11/1995 |
| WO | WO 01/85797 | 11/2001 |
| WO | WO 2004/110355 | 12/2004 |
| WO | WO 2010/008588 | 1/2010 |

OTHER PUBLICATIONS

Alleti et al., "A solanesol-derived scaffold for multimerization of bioactive peptides," J. Org. Chem., 2010, 75(17):5895-5903.
Andreola et al., "DNA aptamers selected against the HIV-1 RNase H display in vitro antiviral activity," Biochem., 2001, 40:10087-10094.
Banga, "Theme section: transdermal delivery of proteins," Pharm. Res., 2007, 24:1357-1359.
Bates, "Treatment effects of immunomodulatory therapies at different stages of multiple sclerosis in short-term trials," Neurol., 2011, 76:S14-25.
Bieber et al., "Human antibodies accelerate the rate of remyelination following lysolecithin-induced demyelination in mice," Glia, 2002, 3:241-249.
Campagnoni, "Molecular biology of myelin proteins from the central nervous system.," J. Neurochem., 51(1): 1-14, 1988.
Compston and Coles, "Multiple sclerosis," Lancet, 2002, 359:1221-1231.
Dougan et al., "Extending the Lifetime of Anticoagulant Oligodeoxynucleotide Aptamers in Blood," Nuclear Med Biol., 2000, 27:289-297.
European Search Report for App. No. 12777569 dated Nov. 10, 2014, 11 pages.
Freedman, "Long-term follow-up of clinical trials of multiple sclerosis therapies," Neurol., 2011, 76:S26-34.
Goebel and Neubert, "Dermal peptide delivery using colloidal carrier systems," Skin Pharmacol. Physiol., 2008, 21:3-9.
Govan et al., "Stabilization and Photochemical Regulation of Antisense Agents through PEGylation," Bioconjugate Chem., 2011, 22(10):2136-2142.
Griffin et al., "The discovery and characterization of a novel nucleotide-based thrombin inhibitor," Gene, 1993, 137:25-31.
Huisgen, "1,3-Dipolar Cycloadditions. Past and Future," Angew Chem. Int. Ed., 1963, 2:565-598.
International Preliminary Report on Patentability in International Application No. PCT/US2012/035005, dated Oct. 29, 2013, 6 pages.
International Search Report and Written Opinion in International Application No. PCT/US2012/035005, dated Nov. 12, 2012, 10 pages.
Ishiguro et al., "Therapeutic Potential of Anti-Interleukin-17A Aptamer," Arthritis Rheumatism, Feb. 2011, 63(2):455-466.
Malik et al., "Recent advances in protein and peptide drug delivery systems," Curr. Drug Deliv., 2007, 4:141-151.
Mayr et al., "Incidence and prevalence of multiple sclerosis in Olmsted County, Minnesota, 1985-2000," (2003) Neurol. 61:1373-1377.

(Continued)

*Primary Examiner* — Sean McGarry
(74) *Attorney, Agent, or Firm* — Fish & Richardson P.C.

(57) ABSTRACT

Materials and methods related to using multimeric DNA aptamers to treat demyelinating diseases are provided herein.

10 Claims, 11 Drawing Sheets

(56) References Cited

OTHER PUBLICATIONS

McGavern et al., "Quantitation of Spinal Cord Demyelination, Remyelination, atrophy, and Axonal Loss in a Model of Progressive Neurologic Injury," *J Neurosci.*, 58(4):492-504, Nov. 15, 1999.

Mitsunaga et al., "Direct evidence that a human antibody derived from patient serum can promote myelin repair in a mouse model of chronic-progressive demyelinating disease," *FASEB J.*, 16(10):1325-1327, Aug. 2002.

Nastasijevic et al., "Remyelination induced by a DNA aptamer in a mouse model of multiple sclerosis," PLoS One, Jun. 2012, 7(6):e39595, 8 pages.

Nastasijevic et al., "Sequence-specific binding of DNA and RNA to immobilized Nickel ions," Biochem. Biophys. Res. Commun., 2008, 366:420-425.

Noseworthy et al., "Multiple sclerosis," New Engl. J. Med., 2000, 343:938-952.

Prausnitz, "A peptide chaperone for transdermal drug delivery," Nat. Biotechnol., 2006, 24:416-417.

Rodriguez et al., "Immune Response Gene products (Ia antigens) on glial and endothelial cells in virus-induced demyelination," *J. Immunol.*, 138(10):3438-3442, May 15, 1987.

Rodriguez et al., "Immunoglobulins reactive with myelin basic protein promote CNS remyelination," *Neurology*, 46(2):538-545, Feb. 1996.

Rodriguez, "Impairment, disability, and handicap in multiple sclerosis: a population-based study in Olmsted County, Minnesota," Neurol., 1994, 44:28-33.

Rostovtsev et al., "A stepwise huisgen cycloaddition process: copper(I)-catalyzed regioselective "ligation" of azides and terminal alkynes," Angew Chem. Int. Ed., 2002, 41:2596-2599.

Shchepinov, "Oligonucleotide Dendrimers: from Polylabelled DNA Probes to Stable Nano-Structures," Glen Report, Nov. 1999, 12(1):1-4.

Soldan et al., "Remyelination-promoting antibodies activate distinct Ca2+ influx pathways in astrocytes and oligodendrocytes: relationship to the mechanism of myelin repair," Mol. Cell. Neurosci., 2003, 22:14-24.

Somasunderam et al., "Combinatorial selection, inhibition, and antiviral activity of DNA thioaptamers targeting the RNase H domain of HIV-1 reverse transcriptase," Biochemistry, 2005, 44:10388-10395.

The Glen Report, "An Unnatural Base Pair System for the Expansion of Genetic Information," May 2008, 20(1):1-3.

Wang et al., "Aptamer antagonists of myelin-derived inhibitors promote axon growth," *PLoS One*, 5(3):e9726, 8 pages, Mar. 16, 2010.

Wang et al., "Inhibition of midkine alleviates experimental autoimmune encephalomyelitis through the expansion of regulatory T cell population," *Proc Natl Acad Sci U S A.*, 105(10):3915-3920, Epub Mar. 4, 2008.

Warrington et al., "Human monoclonal antibodies reactive to oligodendrocytes promote remyelination in a model of multiple sclerosis," Proc. Natl. Acad. Sci. USA, 2000, 97:6820-6825.

Wermeling et al., "Microneedles permit transdermal delivery of a skin-impermeant medication to humans," Proc. Natl. Acad. Sci. USA, 2008, 105:2058-2063.

Wright et al., "Aptamers selected from myelin substrates used as alternatives to antibodies to study, diagnose and treat demyelinating diseases," 29th Annual Meeting of the American Society for Neurochemistry, Mar. 1-5, 2008, 1 page.

Wright et al., "Aptamers selected from myelin substrates used as alternatives to antibodies to study, diagnose and treat demyelinating diseases," J Neurochem., 2008, 104(Suppl. 1):120 (Abstract PTWO5-16).

Yim et al., "Synthesis of DOTA-conjugated multimeric [Tyr$^3$]octreotide peptides via a combination of Cu(I)-catalyzed "click" cycloaddition and thio acid/sulfonyl azide "sulfo-click" amidation and their in vivo evaluation," J. Med. Chem., 2010, 53(10):3944-3953.

\* cited by examiner

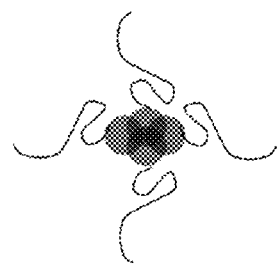
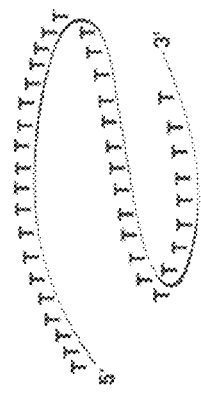
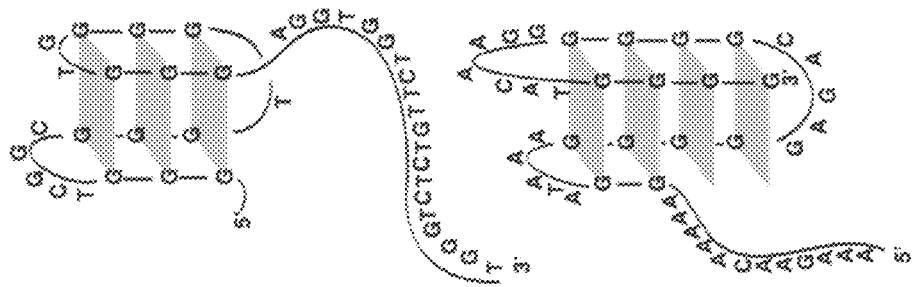
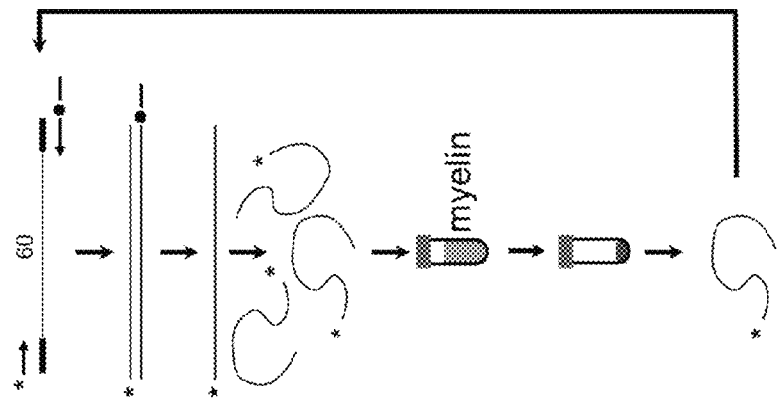

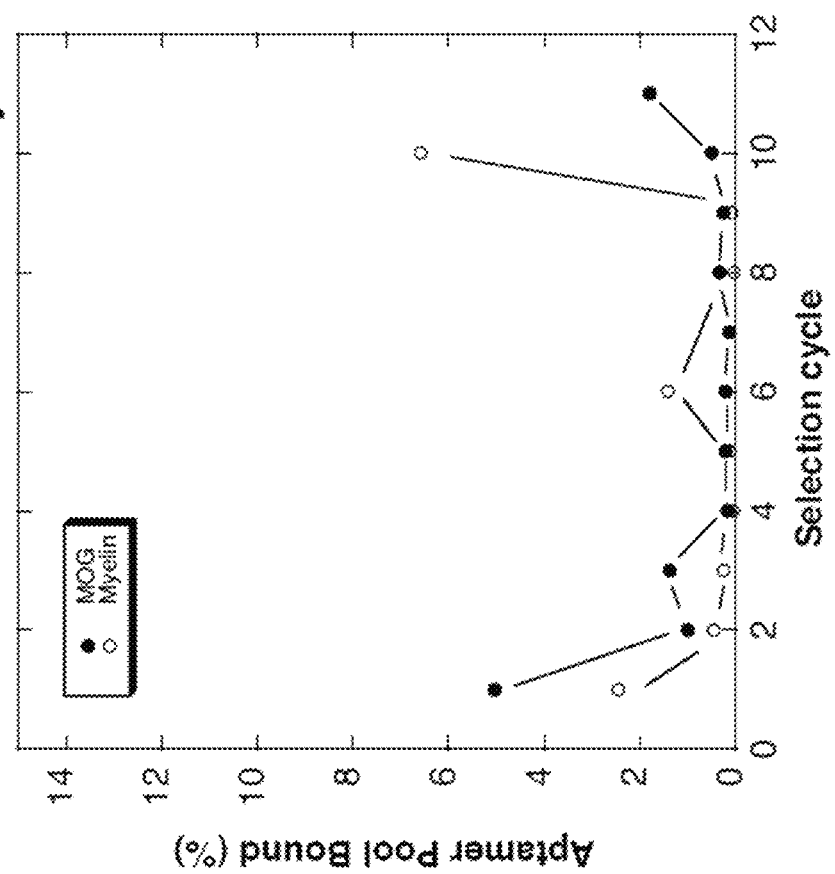

Figure 4

```
ATACCAGCTTATTCAATTGGGTCGGCGGGTGGGGTGGGAGGTGGTCTTGNCTCTGGGTTTTGTTGTGAACNACGCGTNAGATAGTAAGTGCAATCT    (SEQ ID NO:3)
ATACCAGCTTATTCAATTGGGTCGGCGGGTGGGGTGGGNGGAGGTGGTGGTCTTGTCTCTGGGTTTTGTTGTGAACCACGCGTNAGATAGTAAGTGCAATCT    (SEQ ID NO:4)
ATACCAGCTTATTCAATTGGGTCGGCGGGTCGGCGGGTGGGGTGGGAGGTGGTCTTGTCTCTGGGTTTGTTGTGAACCACGCGTAAGATAGTAGTAAGTGCAATCT    (SEQ ID NO:5)
ATACCAGCTTATTCAATTGGGGGGGAGGGGCTAGCCCGNGGGNGACCCCGGAGTGTGGAGACCGTGGTGCTNAGATAGTAAGTGCAATCT    (SEQ ID NO:6)
ATACCAGCTTATTCAATTGTGGGGGGGAGGGGCGGGGTGAGGGCCAGGTGGTCGGTCCAATAAAGCGTCGATGGCNCCAGATAGTAAGTGCAATCT    (SEQ ID NO:7)
ATACCAGCTTATTCAATTGACAGGCGGGGATGAGGGGTTGNCCGGGCGAACATGGGTGCCGAACATGGGGTGGTCAGTCNGTGGNTAAAACCCAAGATAGTAAGTGCAATCT    (SEQ ID NO:8)
ATACCAGCTTATTCAATTGATATGAGGGGGTTGGGAGGTGGAGGATAATNNGGGAGGCGGGTGGTCGTCCAAACAGCTGCCAAGATAGTAAGTGCAATCT    (SEQ ID NO:9)
ATACCAGCTTATTCAATTCCGGTTGGGAGGTGGAGGATAATNNGGGAGGCGGGTGGTCGTCCAAACAGCTGCCAAGATAGTAAGTGCAATCT    (SEQ ID NO:10)
ATACCAGCTTATTCAATTACAACACAGTCTANCCGACAAACCATCTATCTCGATCTATGCAATGAACACACCACTTCCCGCNTANAGATAGTAAGTGCAATCT    (SEQ ID NO:11)
ATACCAGCTTATTCAATTAACGAGGGGGGTGGGGCGAGGGTGGGGGNAAGAAAGCTGGGGGGTCGGNGATGGTAGGCAGGGTCTGAATCGTGTTCGGCAGATAGTAAGTGCAATCT    (SEQ ID NO:12)
ATACCAGCTTATTCAATTTCNGGGCCGAGGGTGGGGNAAGAAAGCTGGGGGGTAGGCAGGGTCGGNGATGGTATGCGCCGGGTTCTAGATAGTAAGTGCAATCT    (SEQ ID NO:13)
ATACCAGCTTATTCAATTATGGGAANAGGGTTGGCCGGGGGGAGAGAGAGGAGGTCGGNGATGCGAGGAGCAACATACGTGCCGAGATAGTAAGTGCAATCT    (SEQ ID NO:14)
ATACCAGCTTATTCAATTGGAANGGTTGGAGGGCTGGNCNATGTGAGACCGGGGGAGGAGCAACATACGTGCCGAGATAGTAAGTGCAATCT    (SEQ ID NO:15)

ATACCAGCTTATTCAATTGGGTCGGCGGGTCGGCGGGTGGGGTGGGTGGGAG (3063; SEQ ID NO:16)
ATACCAGCTTATTCAATTGGGTCGGCGGGTCGGCGGGTGGGGTGGGAG (3028; SEQ ID NO:5)
                               GGGTCGGCGGGTGGGGTGGGTGGGAGGTGGTCTTGTCTCTGGGTTTTGTTGTCTCTGGGT (3064; SEQ ID NO:17)
                                       GTGGTCTTGTCTCTGGGTTTTGTTGTGAACCACACGTAAG (3065; SEQ ID NO:18)
                                                      GTTTTGTTGTGAACCACACGTAAGATAGTAAGTGCAATCT (3066; SEQ ID NO:19)
```

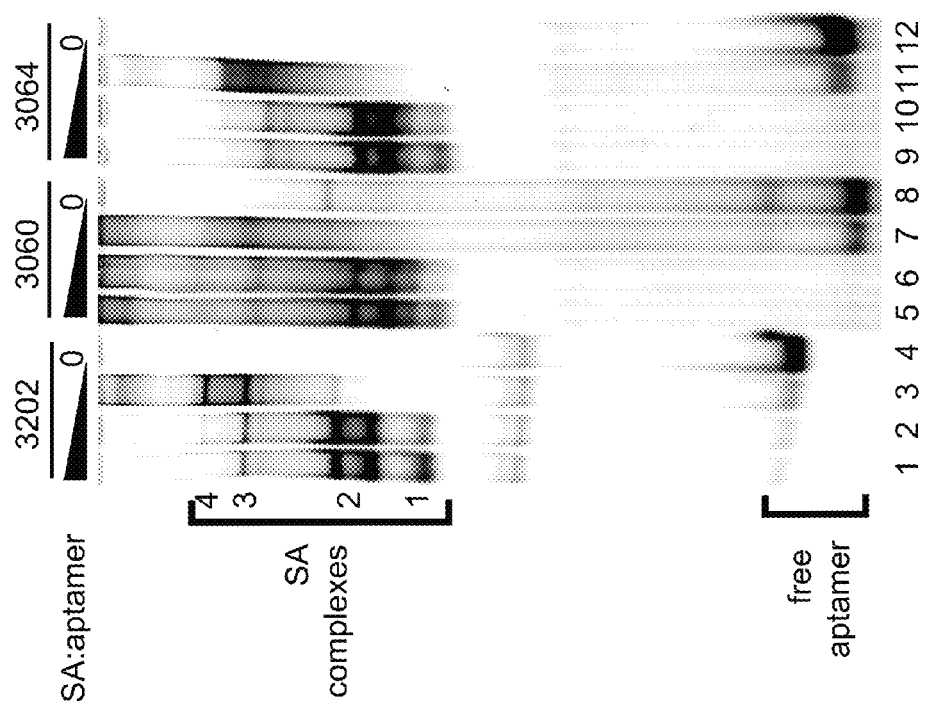

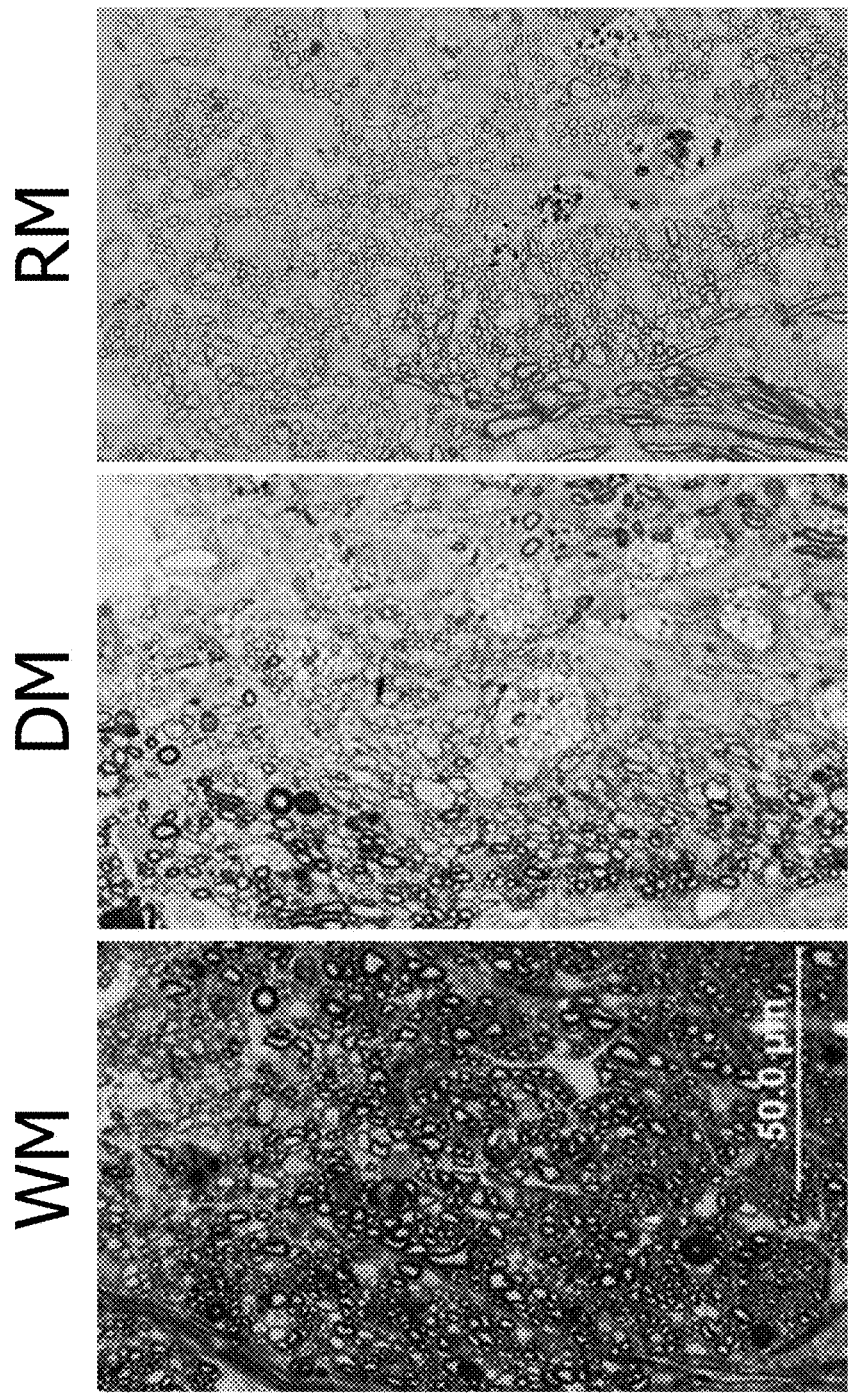

DNA APTAMERS FOR PROMOTING REMYELINATION

CROSS-REFERENCE TO RELATED APPLICATIONS

This application is a continuation application of U.S. Ser. No. 14/837,513, filed Aug. 27, 2015 (now U.S. Pat. No. 9,481,887), which is a continuation of U.S. Ser. No. 14/114,392, filed on Dec. 23, 2013 (now U.S. Pat. No. 9,150,867), which is a National Stage application under 35 U.S.C. §371 of International Application No. PCT/US2012/035005, having an International Filing Date of Apr. 25, 2012, which claims benefit of priority from U.S. Provisional Application Ser. Nos. 61/565,144, filed on Nov. 30, 2011, and 61/480,179, filed Apr. 28, 2011, each of which is incorporated herein by reference in its entirety.

TECHNICAL FIELD

This document relates to materials and methods for reducing demyelination and promoting remyelination, and to the use of multimeric DNA aptamers to treat demyelinating disease.

BACKGROUND

Multiple sclerosis (MS) is a debilitating inflammatory disease of the central nervous system (CNS) that is characterized by local destruction of the insulating myelin surrounding neuronal axons (Compston and Coles (2002) *Lancet* 359:1221-1231). With more than 200 million MS patients worldwide, there is great need for effective treatments that prevent progression or induce repair. Anti-inflammatory therapies have met with some success in preventing relapses (Bates (2011) *Neurol.* 76:S14-25). Some naturally occurring IgM antibodies identified from human serum can promote both cell signaling and remyelination of CNS lesions in an MS model involving chronic infection of susceptible mice by Theiler's encephalomyelitis virus (Warrington et al. (2000) *Proc. Natl. Acad. Sci. USA* 97:6820-6825) and in the lysolecithin model of focal demyelination (Bieber et al. (2002) *Glia* 3:241-249). This result raised the possibility that molecules with binding specificity for oligodendrocytes or myelin components may promote therapeutic remyelination in MS.

SUMMARY

This document is based in part on the identification of a 40-nucleotide, single-stranded DNA aptamer that has affinity for murine myelin and can promote remyelination in a model of MS. As described below, the aptamer can bind to myelin in vitro and in live cerebellar cultures. Peritoneal injection of a formulation containing the aptamer promoted remyelination of CNS lesions in mice infected by Theiler's virus. Interestingly, the DNA aptamer contains guanosine-rich sequences predicted to induce intramolecular folding or intermolecular assembly involving guanosine quartet structures. Relative to monoclonal antibodies, DNA aptamers are small, stable, and non-immunogenic, suggesting new possibilities for MS treatment.

In one aspect, this document features a method for promoting neuronal remyelination in a subject in need thereof. The method can include administering to the subject a pharmaceutical composition comprising a multimeric nucleic acid aptamer in an amount effective to promote remyelination. The nucleic acid aptamer can be a homotetramer. The nucleic acid aptamer can have the sequence set forth in SEQ ID NO:17. The remyelination can be mediated by central nervous system-type myelin producing cells (oligodendrocytes) or mediated by peripheral nervous system-type myelin producing cells (Schwann cells). The subject can be diagnosed with a demyelinating disease (e.g., a demyelinating disease selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease).

In another aspect, this document features a composition containing a pharmaceutically acceptable carrier and a nucleic acid aptamer containing the sequence set forth in SEQ ID NO:17. The nucleic acid aptamer can be a homotetramer.

In another aspect, this document features the use of a multimeric nucleic acid aptamer in the treatment of a demyelinating disease. The multimeric nucleic acid aptamer can contain the sequence set forth in SEQ ID NO:17. The multimeric nucleic acid aptamer can be a homotetramer. The demyelinating disease can be selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease.

This document also features the use of a multimeric nucleic acid aptamer in the preparation of a medicament for treating a demyelinating disease. The multimeric nucleic acid aptamer can contain the sequence set forth in SEQ ID NO:17. The multimeric nucleic acid aptamer can be a homotetramer. The demyelinating disease can be selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-E are schematics showing steps in the selection of DNA aptamers specific for components of crude mouse myelin suspension. FIG. 1A: A pool of about $10^{15}$ 100-nucleotide fluorescent (*) single-stranded DNA aptamers containing 60 nucleotides of random sequence was generated by a PCR and mixed with a suspension of crude mouse myelin. Cycles of affinity purification and amplification yielded a myelin-specific DNA aptamer. FIG. 1B: Deoxyguanosine-rich DNA aptamer 3064 (SEQ ID NO:17) specific for crude mouse myelin is shown folded as a putative intramolecular G-quadruplex. FIG. 1C: Tetravalent complex of 3'-biotinylated DNA aptamer (thin lines) with streptavidin (circles). FIG. 1D: Negative control deoxyguanosine-rich DNA aptamer 3060 (SEQ ID NO:20) specific for chelated nickel ions, shown as putative intramolecular G-quadruplex. FIG. 1E: Negative control oligodeoxythymidylate aptamer 3202 (SEQ ID NO:21).

FIG. 2A shows the 5'-fluorescein modification that was used for in vitro selection and binding studies. FIG. 2B shows the 3' biotin modification that was present in aptamers used for in vivo injection.

FIG. 3 is a graph plotting the results of in vitro selection of DNA aptamer pools over 10-11 rounds of selection and amplification. Targets were myelin oligodendrocyte glycoprotein (MOG) immobilized on Ni-NTA magnetic beads (filled circles) or suspension of crude mouse myelin in buffer (open circles). MOG selections gave rise to aptamer 3060 (selective for chelated Nickel beads). Myelin selections gave rise to aptamer 3064.

FIG. 4 shows the nucleotide sequences of anti-myelin DNA aptamers and derived sub-sequences. The top panel shows initial sequences of DNA aptamers after cloning. Sequences derived from random regions are in regular font. Fixed sequences for PCR primer binding are underlined. The top three sequences correspond to aptamer 3028. The bottom panel shows the sequences of aptamer sub-sequences derived from anti-myelin aptamer 3028.

FIG. 8 is an image showing formation of 3'-biotinylated DNA aptamer multimers by incubation with streptavidin. The indicated 5'-fluoresceinated, 3'-biotinylated DNA aptamers (lanes 4, 8, and 12) were folded and then incubated with different amounts of streptavidin to produce multimeric aptamer complexes. Aptamer:streptavidin concentration ratios were 1:1 (lanes 1, 5, and 9), 4:1 (lanes 2, 6, and 10), and 20:1 (lanes 3, 7, and 11). Mobilities of aptamer monomer and complexes containing one to four aptamers (1-4) are indicated. Complexes with two bound aptamers displayed two distinct mobilities due to cis vs. trans binding arrangements on the streptavidin tetramer.

FIG. 9A is a series of three representative neuropathology micrographs from spinal cords of mice infected with Theiler's virus and treated with various aptamers. Left panel: normal appearing white matter (WM). Center: demyelination (DM). Right: remyelination (RM). After blinded micrograph review of specimens from control and aptamer-treated animals, the percent of spinal cord quadrants showing demyelination or remyelination was determined. Results are reported in Table 1 herein.

DETAILED DESCRIPTION

Figure 2A:
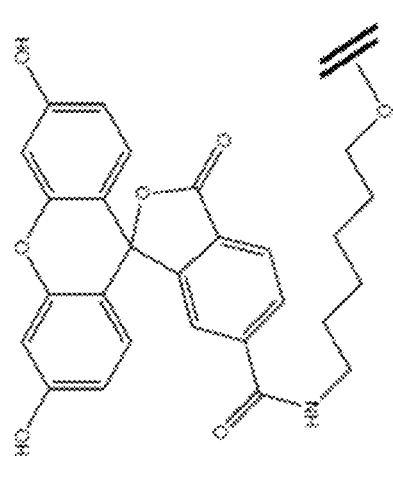
FIGS. 2A-B are diagrams showing chemical modifications of DNA aptamers relevant to the work described herein.

MS is a debilitating neurological disease with a prevalence of about 0.1% in the Western world (Mayr et al. (2003) *Neurol.* 61:1373-1377). MS is fundamentally an inflammatory disease that leads to CNS lesions characterized by the loss of myelin required for electrical insulation of neuronal axons (Noseworthy et al. (2000) *New Engl. J. Med.* (2000) 343:938-952). The resulting symptoms, including fatigue, gait impairment, cognitive impairment, and vision loss, can lead to permanent disability (Rodriguez (1994) *Neurol.* 44:28-33).

While the origin of MS remains unresolved, therapy and cure present even greater challenges. Therapies for relapsing MS include plasma exchange to remove pathogenic immunoglobulins and/or treatment with anti-inflammatory drugs such as glatiramer acetate, β interferon, mitoxantrone, and natalizumab (Bates, supra). These approaches are not curative, and are ineffective in some cases (Freedman (2011) *Neurol.* 76:S26-34). It remains unclear whether curative therapy should be directed against the immune system, or toward repair and rescue of oligodendrocytes and myelin.

Previous studies identified multiple natural murine and human IgM autoantibodies that can bind to live cerebellum and cultured oligodendrocytes and promote remyelination in mice (Warrington et al., supra). Target antigens are not known in molecular detail, but the pentavalent character of the IgM antibody is important for activity (Paz Soldan et al. (2003) *Mol. Cell. Neurosci.* 22:14-24).

This document provides myelin-binding agents that are smaller and more robust than the previously identified IgM monoclonal antibodies. In particular, as described in the Examples below, an in vitro selection method was used to identify small, single-stranded DNA aptamers that have affinity for myelin and that can promote remyelination in mice. Aptamers are folded, single-stranded nucleic acids with activities that, like folded proteins, depend on their three-dimensional shapes and surface features. The advantages of aptamers can, in some embodiments, include one or more of the following: small size, chemical stability, ease of synthesis, lack of immunogenicity, and the availability of in vitro selection technology in which cycles of affinity selection and amplification can be used to identify nucleic acids with rare properties from random libraries that can contain $10^{14}$ or more candidates—chemical diversity exceeding that encoded in mammalian immune systems.

Aptamers useful for promoting remyelination can be about 10 to about 50 nucleotides in length (e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 nucleotides in length, or any range there between), and can include, for example those having the sequences shown in FIG. 4 (SEQ ID NOS:3 to 19) or fragments thereof. An aptamer containing, consisting of, or consisting essentially of the sequence 5'-TACCAGCT-TATTCAATTGGGTCGGCGGGTGGGGTGGGAGGTG-GTCTTGTCTCTGGGTTTTGTTGTGAACCACACG-TAAGATAGTAAGTGCAATCT-3' (SEQ ID NO:5) or 5'-GGGTCGGCGGGTGGGGTGGGAGGTGGTCTT-GTCTCTGGGT-3' (SEQ ID NO:17), or a fragment thereof, can be particularly useful.

A nucleic acid aptamer can be monomeric, or can be multimeric. For example, an aptamer can be a dimer, a trimer, a tetramer, a pentamer, or a hexamer, and can be homomeric or heteromeric. In some embodiments, an aptamer can be configured as a homomultimer. See, for example, the Examples below, which describe the use of a homotetramer containing four copies of SEQ ID NO:17. In some cases, an aptamer can be complexed with another compound that can provide stabilization and/or multimerization. For example, one or more aptamers can be combined using biotin-avidin linkages as described in the Examples, or with polyethylene glycol linkages (see, e.g., Govan et al. (2011) *Bioconjugate Chem.* 22(10):2136-2142). In some embodiments, aptamer synthesis can be performed with a solid support to yield structures in which the aptamers are head-to-head multimers. Synthesis reagents are available commercially (e.g., from Glen Research; Sterling, Va.); see, also Shchepinov (1999) *The Glen Report* 12(1):1-4, available on the World Wide Web at glenresearch.com/GlenReports/GR12-11.html and glenresearch.com/GlenReports/GR12-1.pdf. Further, azide/alkyne 3+2 cycloaddition chemistry can allow for rapid coupling of derivatized oligonucleotides to a central chemical backbone. Such a procedure could be used to create oligonucleotide multimers cleanly and efficiently without a central protein. See, e.g., Rostovtsev et al. (2002) *Angew Chem. Int. Ed.* 41:2596-2599; and Huisgen (1963) *Angew Chem. Int. Ed.* 2:565-598, as well as *The Glen Report* (2008) 20(1):8-9 available on the World Wide Web at glenresearch.com/GlenReports/GR20-14.html and glenresearch.com/GlenReports/GR20-1.pdf. See, also, U.S. Publication No. 2009/0234105; Alleti et al. (2010) *J. Org. Chem.* 75(17):5895-5903; and Yim et al. (2010) *J. Med. Chem.* 53(10):3944-3953.

The aptamers described herein can be used to treat demyelinating diseases (e.g., MS) by inducing remyelination. For example, a nucleic acid aptamer as described herein (e.g., an aptamer having the sequence set forth in SEQ ID NO:17) can be synthesized and formulated into a pharmaceutical composition for administration to a subject diagnosed as having a disorder of the nervous system in which the myelin sheath of neurons is damaged. In addition to MS, demyelinating diseases that can affect the central nervous system include idiopathic inflammatory demyelinating diseases, transverse myelitis, Devic's disease progressive multifocal leukoencephalopathy, optic neuritis, and leukodystrophies and acute disseminated encephalomyelitis (ADEM). Demyelinating diseases that can affect the peripheral nervous system include Guillain-Barré syndrome, chronic inflammatory demyelinating polyneuropathy, anti-MAG peripheral neuropathy, and Charcot-Marie-Tooth disease.

The aptamers described herein can be incorporated into compositions for administration to a subject in need thereof (e.g., a subject identified as having a demyelinating disease). Thus, this document provides, for example, the use of aptamers as described herein in the manufacture of medicaments for treating (e.g., reducing) demyelination and/or enhancing remyelination.

Methods for formulating and subsequently administering therapeutic compositions are well known to those in the art. Dosages typically are dependent on the responsiveness of the subject to the compound, with the course of treatment lasting from several days to several months, or until a suitable response is achieved. Persons of ordinary skill in the art routinely determine optimum dosages, dosing methodologies and repetition rates. Optimum dosages can vary depending on the relative potency of an aptamer, and generally can be estimated based on the $EC_{50}$ found to be effective in in vitro and/or in vivo animal models. Compositions containing the aptamers may be given once or more daily, weekly, monthly, or even less often, or can be administered continuously for a period of time (e.g., hours, days, or weeks). For example, an aptamer or a composition containing an aptamer can be administered to a patient at a dose of at least about 0.01 ng/kg to about 100 mg/kg of body mass.

An aptamer can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some embodiments, a composition can contain an aptamer as provided herein in combination with a pharmaceutically acceptable carrier. Pharmaceutically acceptable carriers include, for example, pharmaceutically acceptable solvents, suspending agents, or any other pharmacologically inert vehicles for delivering nucleic acid aptamers to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing aptamers as described herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful. Methods and compositions for transdermal delivery include those described in the art (e.g., in Wermeling et al. (2008) *Proc. Natl. Acad. Sci. USA* 105:2058-2063; Goebel and Neubert (2008) *Skin Pharmacol. Physiol.* 21:3-9; Banga (2007) *Pharm. Res.* 24:1357-1359; Malik et al. (2007) *Curr. Drug Deliv.* 4:141-151; and Prausnitz (2006) *Nat. Biotechnol.* 24:416-417).

Nasal preparations can be presented in a liquid form or as a dry product. Nebulized aqueous suspensions or solutions can include carriers or excipients to adjust pH and/or tonicity.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Compositions provided herein can contain any pharmaceutically acceptable salts, esters, or salts of such esters, or any other compound which, upon administration to a subject, is capable of providing (directly or indirectly) the biologically active aptamer. The term "pharmaceutically acceptable salts" refers to physiologically and pharmaceutically acceptable salts of the nucleic acid aptamers useful in methods provided herein (i.e., salts that retain the desired biological activity of the parent aptamers without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions.

In some cases, an aptamer provided herein can be formulated as a sustained release dosage form. For example, an aptamer can be formulated into a controlled release formulation. In some cases, coatings, envelopes, or protective matrices can be formulated to contain one or more of the polypeptides provided herein. Such coatings, envelopes, and protective matrices can be used to coat indwelling devices such as stents, catheters, and peritoneal dialysis tubing. In some cases, an aptamer provided herein can be incorporated into a polymeric substances, liposomes, microemulsions, microparticles, nanoparticles, or waxes.

Pharmaceutical formulations as disclosed herein, which can be presented conveniently in unit dosage form, can be prepared according to conventional techniques well known in the pharmaceutical industry. Such techniques include the step of bringing into association the active ingredient(s) (i.e., an aptamer) with the desired pharmaceutical carrier(s). Typically, the formulations can be prepared by uniformly and intimately bringing the active ingredient(s) into association with liquid carriers or finely divided solid carriers or both, and then, if necessary, shaping the product. Formulations can be sterilized if desired, provided that the method of sterilization does not interfere with the effectiveness of the molecules(s) contained in the formulation.

The nucleic acid aptamers (e.g., comprising SEQ ID NO:17) provided herein can be administered to a mammal (e.g., a human or a non-human mammal) in order to reduce demyelination that can occur with diseases such as MS, for example. The aptamers can be administered at any suitable dose, depending on various factors including, without limitation, the agent chosen and the patient characteristics. Administration can be local or systemic.

In some embodiments, an aptamer or a composition containing an aptamer can be administered at a dose of at least about 0.01 ng/kg to about 100 mg/kg of body mass (e.g., about 10 ng/kg to about 50 mg/kg, about 20 ng/kg to about 10 mg/kg, about 0.1 ng/kg to about 20 ng/kg, about 3 ng/kg to about 10 ng/kg, or about 50 ng/kg to about 100 µg/kg) of body mass, although other dosages also may provide beneficial results.

The methods provided herein can include administering to a mammal an effective amount of an aptamer, or an effective amount of a composition containing such an aptamer. As used herein, the term "effective amount" is an amount of an aptamer or aptamer-containing composition that is sufficient to reduce the occurrence of demyelination or increase the occurrence of remyelination in a mammalian recipient by at least 10% (e.g., 10%, 15%, 20%, 25%, 30%, 40%, 50%, 60%, 70%, 75%, 80%, 85%, 90%, 95%, 99%, or 100%). The presence or extent of demyelination and remyelination can be evaluated using methods known in the art, including, for example, the methods described in the Examples section herein.

In some embodiments, for example, an "effective amount" of an aptamer as provided herein can be an amount that reduces demyelination in a treated mammal by at least 10% as compared to the level of demyelination in the mammal prior to administration of the aptamer, or as compared to the level of demyelination in a control, untreated mammal.

The invention will be further described in the following examples, which do not limit the scope of the invention described in the claims.

EXAMPLES

Example 1

Materials and Methods

Preparation of crude murine myelin: CNS tissue from strain SJL mice (5 g) was homogenized in 0.32 M sucrose containing 2 mM EGTA (pH 7.5) using a tissue grinder, followed by a Dounce homogenizer to yield a final volume of 100 ml. The homogenate (17 ml) was layered onto 3 ml of 0.85 M sucrose containing 2 mM EGTA and subjected to centrifugation at 28,000 rpm for 1 hour at 4° C. Material was collected from the interface and homogenized in a total volume of 240 ml of a solution containing 2 mM EGTA. After centrifugation, the pellet was homogenized in 5 ml of a solution containing 10 mM EGTA, the volume was brought to 400 ml in 10 mM EGTA, and the solution was stirred for 15 minutes at 4° C. After centrifugation for 15 minutes at 10,000 rpm, the homogenization and centrifugation steps were repeated. The resulting pellet was homogenized in 100 ml of solution containing 0.85 M sucrose and 2 mM EGTA. The homogenate was overlayed with 3 ml of a solution containing 0.32 M sucrose and 2 mM EGTA, and subjected to centrifugation at 28,000 rpm for 90 minutes. After repeated homogenization and washing, the myelin was isolated from the 0.32 M/0.75 M interface of a discontinuous sucrose gradient, washed with distilled water, and resuspended in 50 mM Tris-HCl containing 2 mM EGTA.

In vitro selection of DNA aptamers: A random DNA library was created and single-stranded 5'-fluorescein-(FIG. 2A) conjugated oligonucleotides were subjected to in vitro selection for binding to suspensions of crude murine myelin. The initial round of selection employed 2.5 nmole (~1×10$^{15}$ molecules) of random oligonucleotide library LJM-2772. Oligonucleotides were heated to 90° C. for 1 minute in PBS containing 1 mM MgCl$_2$, placed on ice for 15 minutes, and then incubated for 8 minutes at room temperature to allow folding. 200 µL of mouse myelin suspension (10 µg) was pelleted by centrifugation for 5 minutes at 6500 rpm (microcentrifuge). The pellet was washed twice by resuspension in 500 µL binding buffer (20 mM Tris-HCl, pH 7.6, 10 mM NaCl, 0.5 mM KCl). The DNA library (5 µM in the first round, 300 nM in subsequent rounds) was then incubated for 30 minutes with gentle agitation in a 500 µL binding reaction with 10 µg myelin suspension in 500 µL binding buffer. The suspension and bound aptamers were washed twice with 1 mL binding buffer by 6500 rpm centrifugation. To the pellet was added 400 µL 2×PK buffer (300 mM NaCl, 2.5 mM EDTA, 2% SDS), followed by agitation, and extraction with 400 µL phenol:chloroform (1:1, v:v). DNA was precipitated from the aqueous phase by addition of ethanol. A portion of the recovered DNA was amplified by PCR to establish the optimal number of amplification cycles. After the first round, PCR was performed with a fluorescein-labeled primer, allowing quantitation of library recovery by fluorescence spectroscopy. The upper primer sequence was 5'-F-ATACCAGCTTATTCAATT (SEQ ID NO:1; F indicates fluorescein). The lower primer sequence was 5'-AAAAAAAAAAAAAAAAAAAAAXXAGATTGCACTTACTATCT (SEQ ID NO:2; X indicates GLEN Research spacer phosphoramidite 10-1909). PCR reactions (100 µL) employed Taq DNA polymerase, primers at 10 µM final concentration, and incubation for 5 minutes at 94° C., followed by cycles of 30 seconds at 94° C., 30 seconds at 47° C., and 30 seconds at 72° C. A second aliquot of recovered DNA was then amplified for the optimum number of cycles to prepare aptamer for the next selection round. Single-stranded fluorescent aptamer was obtained by precipitation of PCR reactions from ethanol, followed by denaturing polyacrylamide gel electrophoresis. The fluorescent DNA band was cut from the gel, diced, and eluted in TE buffer at 37° C. for 2-12 hours, followed by precipitation from ethanol and quantitation by UV spectrometry. After 11 selection cycles, PCR was performed and the resulting duplex DNA was ligated into the pGEM-Teasy cloning vector (Promega, Madison, Wis.), cloned, and sequenced. An active 40-nucleotide subsequence ("3064," having the sequence 5'-GGGTCGGCGGGTGGGGTGGGAGGTGGTCTTGTCTCTGGGT-3'; SEQ ID NO:17); was identified for further study.

Aptamer specificity characterization: To promote intramolecular folding, aptamer stock solutions (5 µM) in PBS were heated to 90° C., MgCl$_2$ was added to a final concentration of 1 mM, and solutions were allowed to cool room temperature. Myelin stock was diluted in PBS and sonicated on ice. Fluorescent folded aptamers were added to different amounts of myelin suspension and incubated at 37° C. for 3 hours. Insoluble material with bound aptamers was recovered by centrifugation for 30 seconds in a microcentrifuge. The pellet was washed with 100 µL PBS and again recovered by centrifugation. After phenol extraction and ethanol precipitation, fluorescent aptamers were quantitated in black plastic 96-well plates using a Typhoon Fluorescent Imaging system (GE Healthcare Biosciences; Piscataway, N.J.). For Southwestern blotting, 15 µg crude myelin protein was separated in each lane of a 10% Bis-Tris SDS polyacrylamide gel in 2-(N-morpholino)ethanesulfonic acid (MES) buffer. After electrophoresis, duplicate lanes were either stained with Coomassie blue dye or transferred to polyvinylidene fluoride (PVDF) membrane by electroblotting. Western blotting was performed by standard methods using antibodies with the indicated specificities. For southwestern blots, membranes were blocked for 30 minutes at 37° C. in tris-buffered saline and TWEEN® 20 (TBST) buffer containing with 1% bovine serum albumin (BSA), 10% non-fat dry milk, 2 mg/mL sonicated and heat-denatured salmon testis DNA, and TWEEN® 20 detergent. Folded fluorescent aptamers (5 µM final concentration) were then added in PBS containing 1 mM MgCl$_2$ and incubated with PVDF membranes for 14 hours, followed by washing in TBST buffer and then in 0.5× tris/borate/EDTA (TBE) buffer. Fluorescein fluorescence was then detected on membranes using the Typhoon Fluorescent Imaging system. Tryptic peptide mass fingerprinting was performed.

Mouse model: Eight-week-old female SJL/J mice (Jackson Laboratories; Bar Harbor, Me.) received a single intracerebral injection of $2\times10^5$ plaque-forming units of the Daniel's strain of Theiler's Myeloencephilitus Virus (TMEV) in Dulbecco's phosphate buffered saline (DPBS; 10 µL). The resulting encephalitic-like infection resulted in greater than 98% incidence of demyelination with increasing neurologic deficits progressing over several months (Rodriguez et al. (1987) Crit. Rev. Immunol. 7:325-365). Animals used for remyelination studies were chronically demyelinated by six months post infection, with clear neurologic deficits. To assemble treatment groups in cages of five mice each, all mice to be treated were combined in a large container and then distributed equally based on the level of disability. The extent of mouse disability was determined by examination of the mouse coat color, a reflection of the ability to self-groom, gait, and the ability to right when placed on the dorsal side.

Aptamer treatment: DNA oligonucleotides 3064 (SEQ ID NO:17), 3060 (5'-AAAGAACAAAAAGGA-TAAAGGGGGAGACGGGGGGAACATGGGG-3'; SEQ ID NO:20) and 3202 (5'-TTTTTTTTTTTTTTTTTTTTTTTTTTTTTTTTTTTT-3'; SEQ ID NO:21) were synthesized DMT-off at 1 µmol scale using 3' biotinTEG control pore glass support (Glen Research 20-2955). Oligonucleotides were cleaved from the support and deprotected in hot ammonia, then dried and purified by reverse phase HPLC and sterilized by precipitation from ethanol.

Figure 2B:
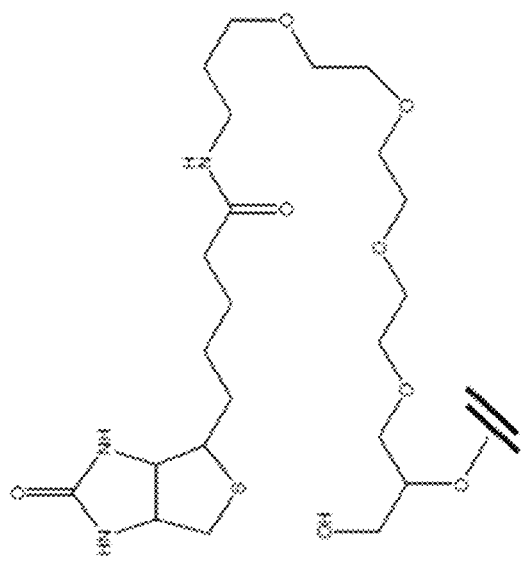
Figure 7:
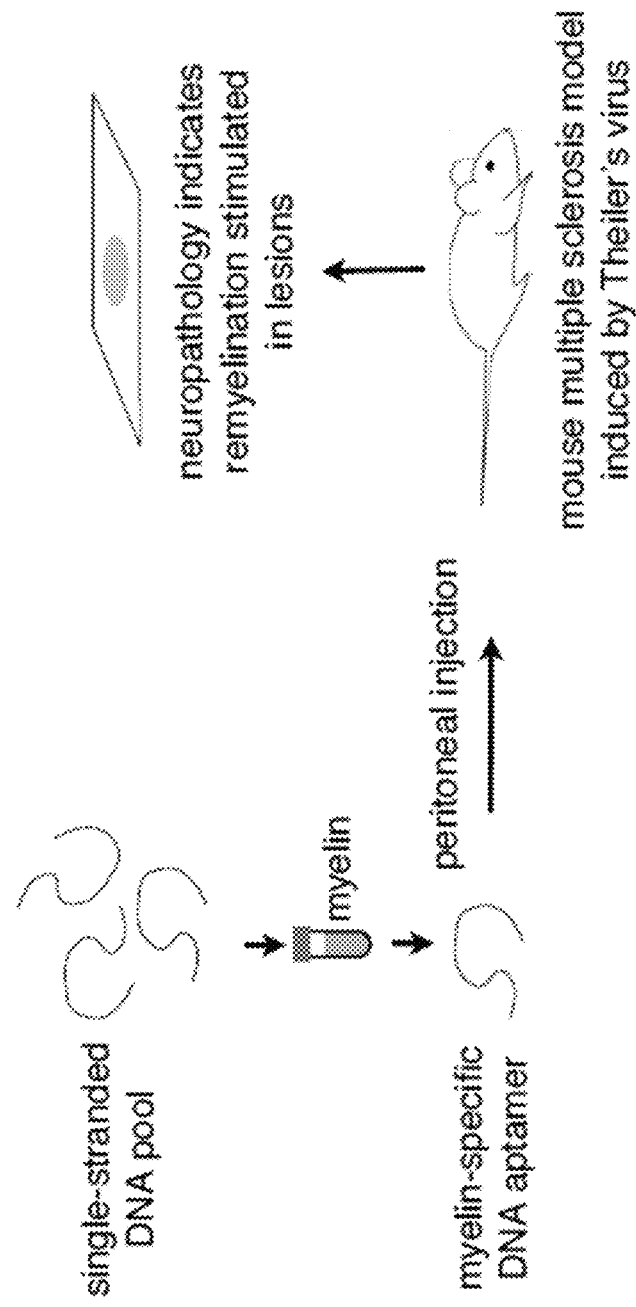
FIG. 7 is a schematic illustrating the experimental approach for in vivo studies. After cloning and identification of the DNA subsequence important for myelin binding, DNA aptamers were injected into the peritoneal cavities of mice with demyelinating CNS lesions induced by Theiler's encephalomyelitis virus infection. Immunopathology at 7-9 months after infection revealed enhanced remyelination.

Demyelinating CNS lesions were induced by infection using Daniel's strain of Theiler's virus in SJL mice (FIG. 7). After 27 weeks, mice were injected intraperitoneally (i.p.) with synthetic DNA aptamers (test sequences or controls) that had been prepared as 3' biotinylated (FIG. 2B) derivatives and mixed with excess streptavidin to promote stability. Groups of mice received i.p. 500-µL injections of the 3' biotin conjugated aptamer (1 µM) combined with streptavidin (0.25 µM) in calcium-free D-PBS (Invitrogen; Carlsbad, Calif.) supplemented with magnesium chloride (1 mM). Injections were given twice per week for five weeks. Briefly, sterile aptamer solution (1 µM) in calcium-free D-PBS supplemented with $MgCl_2$ (1 mM) was heated to 90° C. for 1 minute, placed on ice for 15 minutes, and then incubated for 8 minutes at room temperature to allow aptamer folding. Streptavidin stock solution (Jackson Immune Research; West Grove, Pa.; 1 mg/mL; 18 µM in calcium-free D-PBS) was added to a final concentration of 0.25 µM and incubated with gentle agitation for 30 minutes at 37° C. immediately prior to i.p. injection into mice. The final aptamer injection solution (500 µL) contained streptavidin: 13.8 µg/mL (0.25 µM), aptamer-3'-Biotin: 13.4 (12.7-14.2) µg/mL (1.2-1.5 µM) in calcium-free D-PBS supplemented with $MgCl_2$ (1 mM). Each treatment therefore consisted of 6.9 µg (125 pmol) streptavidin, 6.7 µg (500 pmol) aptamer-3'-biotin, and 47.6 µg (500 µmol) $MgCl_2$. Neuropathology to characterize the extent of lesion remyelination was performed five weeks after completion of aptamer injections according to a blinded protocol.

Spinal cord morphometry: Mice were anesthetized with sodium pentobarbital and perfused intracardially with Trump's fixative (phosphate-buffered 4% formaldehyde/1% glutaraldehyde, pH 7.4). Spinal cords were removed and cut into 1 mm blocks, and every third block was postfixed and stained with osmium tetroxide and embedded in araldite plastic (Polysciences, Warrington, Pa.). One-micrometer-thick cross-sections were cut from each block, mounted onto glass slides, and stained with 4% paraphenylene-diamine to visualize myelin (Rodriguez et al. (1987) J. Immunol. 138: 3438-3442). Ten to twelve spinal cord sections, representing samples from the cervical, thoracic, lumbar, and sacral spinal cord, were stained with 4% p-phenylenediamine to visualize the myelin sheaths, and neuropathology was performed according to a blinded protocol. Sections were analyzed for spinal cord pathology (inflammation, demyelination, remyelination) as previously described (McGavern et al. (1999) J. Neurosci. Res. 58:492-504). Each spinal cord section was divided visually into four quadrants based on morphological symmetry and examined by bright field microscopy at 100× and 200× total magnification using an Olympus Provis microscope. Each quadrant from each section was graded for the presence or absence of gray matter disease, meningeal inflammation, and demyelination. Demyelinated areas were characterized by denuded axons and inflammatory cell infiltrates. Demyelinated areas with remyelination were characterized by thin myelin sheaths compared with the thicker, intact myelin sheaths. The spinal cord white matter was scored as normal, demyelinated with no remyelination, or demyelinated with remyelination (Mitsunaga et al. (2002) FASEB J. 16:1325-1327). Partial quadrants were excluded. Lesions were judged to be remyelinated when they were 75-100% repaired. Remyelinated lesions below this threshold were scored as negative. Data were not assembled into treatment groups until all slides in a given study were graded. Demyelination for each mouse was calculated as a percentage based on the number of spinal cord quadrants with demyelination, which included quadrants with demyelination and repair, divided by the total number of quadrants scored. Remyelination for each mouse was calculated as a percentage based on the number of demyelinated quadrants above threshold remyelination divided by the number of quadrants with demyelination. Data for percentage spinal cord demyelination and remyelination were compared across groups using one-way ANOVA on ranks. When a significant difference (P<0.05) was identified, a pairwise comparison of aptamer-treated groups with the aptamer-control and untreated control groups was performed. Statistical analysis and plots were performed using SigmaStat and SigmaPlot. Data are presented as mean±SEM.

Example 2

Identification and Characterization of Aptamers that Bind Murine Myelin

In vitro selection from a single-stranded DNA library was used to identify aptamers that bound to a suspension of crude murine myelin (FIG. 1A). The results of in vitro selection of DNA aptamer pools over 10-11 rounds of selection and amplification are plotted in FIG. 3. Targets were myelin oligodendrocyte glycoprotein (MOG) immobilized on Ni-NTA magnetic beads (filled circles) or suspension of crude mouse myelin in buffer (open circles). These procedures yielded a set of DNA molecules that were sequenced (FIG. 4). MOG selections gave rise to aptamer 3060 (selective for chelated Nickel beads; FIG. 1D; SEQ ID NO:20). Myelin selections gave rise to aptamer 3064 (FIGS. 1B, 1C and 4; SEQ ID NO:17).

The anti-myelin aptamer 3064 was compared with negative control aptamers 3060 and 3202 (SEQ ID NOS:20 and 21; FIGS. 1D and 1E). Interestingly, as observed for some other DNA aptamers (Griffin et al. (1993) Gene 137:25-31;

and Somasunderam et al. (2005) *Biochemistry* 44:10388-10395; Andreola et al. (2001) *Biochemistry* 40:10087-10094), both aptamer 3064 (specific for myelin) and control aptamer 3060 (selected for affinity to chelated nickel ions; Nastasijevic et al. (2008) *Biochem. Biophys. Res. Commun.* 366:420-425) contain guanosine-rich domains predicted to induce intra- or intermolecular folding through guanosine quartets.

Figure 5A:
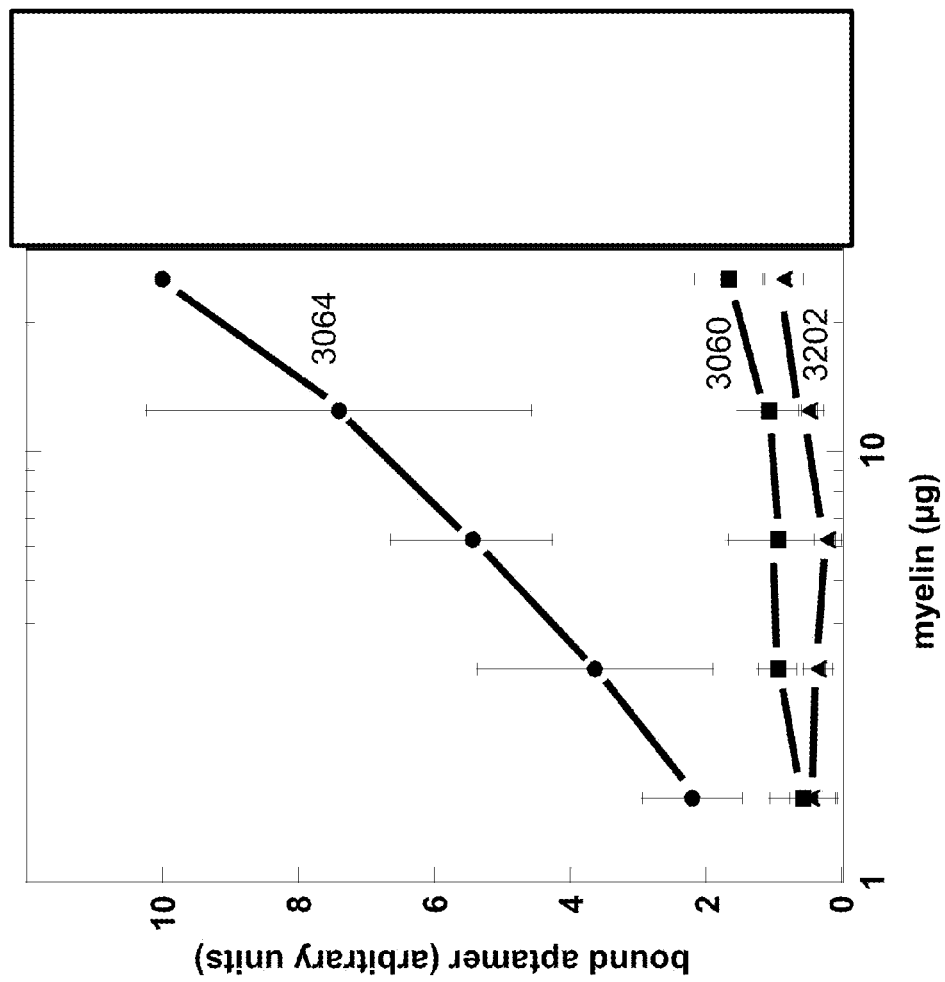
FIG. 5A is a graph plotting binding of fluorescent aptamers 3064 (filled circles), 3060 (filled squares), and 3202 (filled triangles) to crude mouse myelin proteins as detected by sedimentation of the insoluble myelin fraction. Mean and standard deviation are shown for three experiments.
Figure 5B:
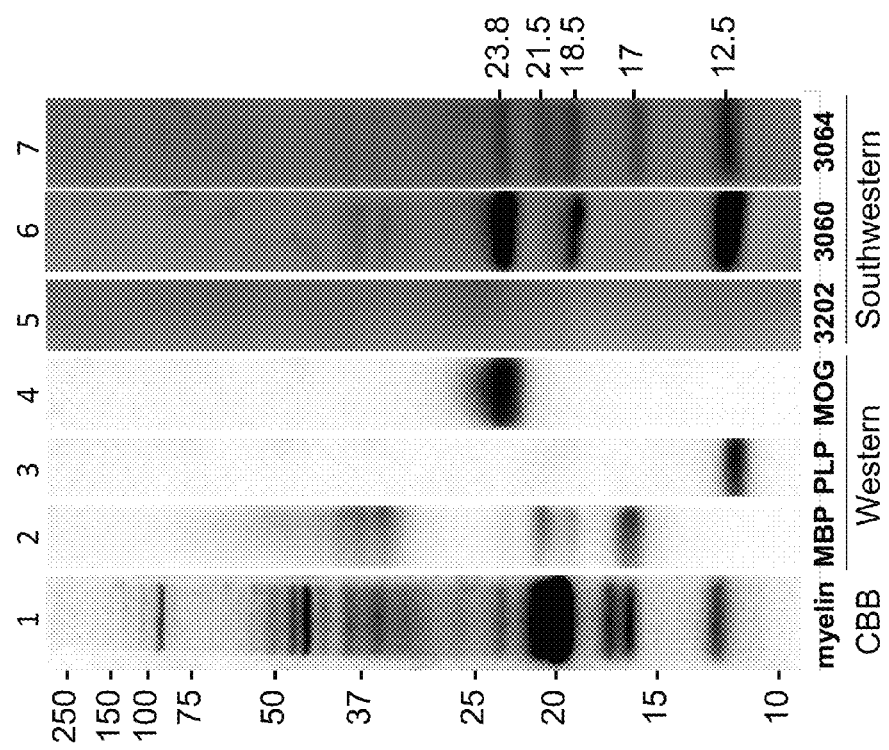
FIG. 5B is an image showing lanes from gels and blots demonstrating DNA aptamer specificity. Lane 1: Coomassie staining of crude myelin proteins (myelin; CBB) separated by SDS-polyacrylamide gel electrophoresis. Lanes 2-7: results of western and southwestern blotting with the indicated antibodies or fluorescent aptamers. Mobilities of molecular weight standards are indicated at left, and apparent molecular weights of aptamer-reactive proteins are indicated at right.

The specificity of anti-myelin DNA aptamer 3064 and controls 3060 and 3202 was analyzed by assessing the binding of fluorescent aptamers to crude myelin protein suspension using centrifugal sedimentation to recover bound aptamers (FIG. 5A). Myelin-specific aptamer 3064 showed strong myelin-dependent binding, while aptamers 3060 and 3202 did not. Because the myelin preparation was a crude mixture of proteins and lipids, however, these results did not provide quantitative affinity estimates. To further assess specificity, crude myelin proteins were separated by SDS-polyacrylamide gel electrophoresis and stained with Coomassie dye (myelin; FIG. 5B, left lane), or blotted to polyvinylidene (PVDF) membrane and probed with antibodies against myelin basic protein (MBP), proteolipid protein (PLP), or MOG in western blots (FIG. 5B, lanes 2-4), or probed with fluorescent aptamers 3202, 3060 or 3064 in southwestern blots (FIG. 5B, lanes 5-7). While control aptamer 3202 showed no binding to myelin proteins, guanosine-rich aptamers 3060 and 3064 bound specifically to certain proteins (FIG. 5B). In particular, control aptamer 3060 and myelin-specific aptamer 3064 both bound to three myelin proteins with apparent molecular weights of 12.5 kDa, 18.5 kDa, and 23.8 kDa. Based on western analysis and mass spectrometry of tryptic peptides, these proteins were PLP, the 18.5 kDa isoform of MBP, and MOG, respectively. Myelin-specific aptamer 3064 uniquely bound to myelin proteins with apparent molecular weights of 17 kDa and 21.5 kDa, identified as MBP isoforms containing sequences encoded by MBP exon 2 (Campagnoni (1988) *J. Neurochem.* 51: 1-14).

DNA aptamer 3064 was observed to bind preferentially to an intact myelin suspension (FIG. 5A), while both aptamers 3060 and 3064 showed affinity for certain myelin proteins after extraction of lipids and immobilization (FIG. 5B). These results suggested that MBP sequences encoded in exon 2 were targeted by aptamer 3064, and these sequences were preferentially accessible in crude myelin suspensions. Extraction of proteins for Southwestern blotting revealed other aptamer binding sites that may not be accessible in intact myelin.

Figure 6:
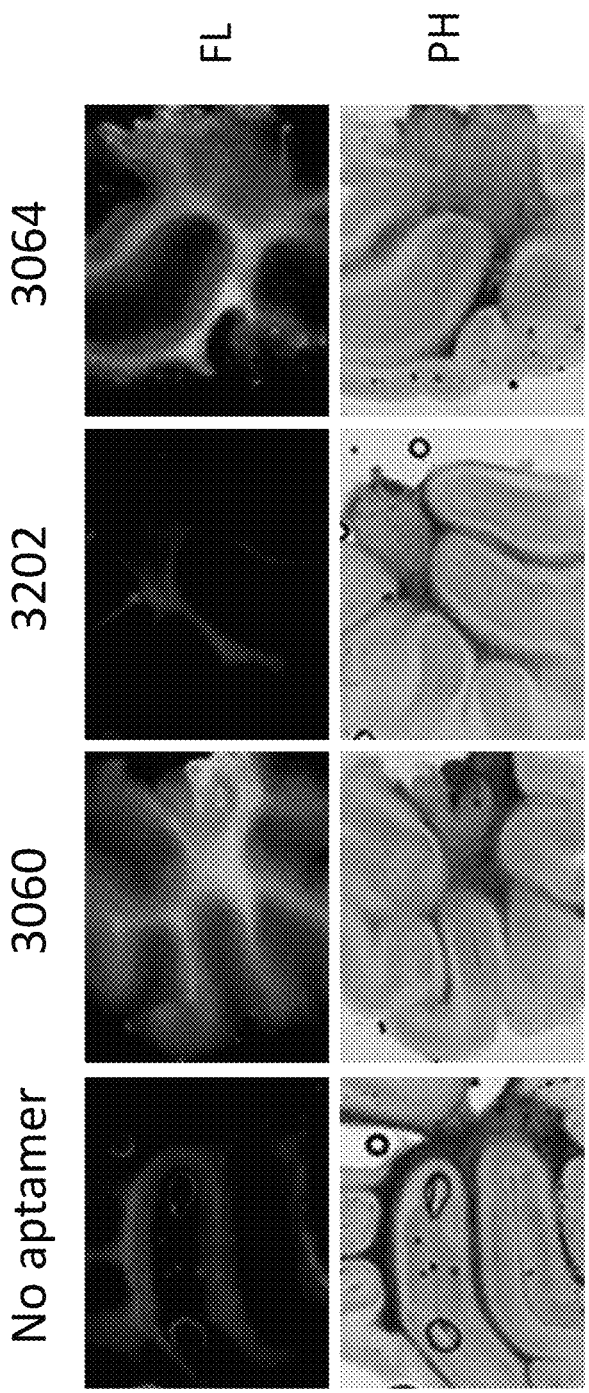
FIG. 6 is a series of images showing aptamer staining of unfixed cerebellar slices. Live mouse cerebellar slices were incubated with 1 μM fluorescein labeled aptamer in PBS for 30 minutes on ice. The tissue was then washed, fixed with 4% paraformaldehyde and mounted. Binding of the fluorescein-labeled aptamers to myelin rich regions of the cerebellum was detected as fluorescein epi-fluorescence images with an Olympus DP-70 camera (FL, upper panels). Matching phase contrast images are shown in the lower panels (PH). Background fluorescence showed no specific signal. Aptamer 3060 (nickel specificity) showed diffuse binding throughout the molecular cell layer of the cerebellum. Aptamer 3064 demonstrated myelin specific binding to white matter tracts of the cerebellum. Control aptamer 3202 (poly-dT) showed less binding.

The specificity of anti-myelin DNA aptamer 3064 and controls 3060 and 3202 also was analyzed by assessing binding of fluorescent aptamer derivatives to living murine cerebellar sections (FIG. 6). Negative control aptamer 3202 showed little or no binding to cerebellar sections, control aptamer 3060 bound diffusely to white matter, and anti-myelin aptamer 3064, which bound to crude myelin in vitro, strongly bound myelin-rich regions of the brain (FIG. 6).

Example 3

In vivo Enhancement of Remyelination by DNA Aptamer Treatment

The binding properties of anti-myelin DNA aptamer 3064 were similar to certain natural human IgM autoantibodies that promote remyelination in the murine Theiler's encephalomyelitis virus model of MS (Warrington et al., supra). Intraperitoneal injection of anti-myelin DNA aptamer 3064 therefore was compared to negative control aptamers 3060 and 3202. Aptamers were prepared as 3'-biotin conjugates (FIG. 2B) and incubated in a 4:1 molar ratio with tetrameric streptavidin to create conjugates with enhanced stability and biodistribution (Dougan et al. (2000) *Nuclear Med. Biol.* 27:289-297), mimicking polyvalent antibodies. As shown in FIG. 8 (lanes 2, 6, and 10), 4:1 aptamer:streptavidin incubation under these conditions converted all monomeric aptamers to streptavidin complexes, predominantly dimers.

Aptamers were injected into mice 27 weeks after Theiler's virus infection, and CNS pathology was assessed by blinded review of neuropathology after 5 weeks. Results are shown in Table 1 and FIG. 9A. Anti-myelin DNA aptamer 3064 induced remyelination (with at least 75% of the lesion being remyelinated) in 26% of experimental CNS lesions, compared to 8% and 4% for negative control aptamers 3060 and 3202, respectively. These statistically significant results indicated selective enhancement of remyelination in vivo by anti-myelin DNA aptamer treatment.

TABLE 1

Remyelination in vivo after DNA aptamer treatment

| Aptamer (specificity) | $n^1$ | Quadrants with demyelination(%) | Demyelinated quadrants with remyelination (%) |
|---|---|---|---|
| 3060 (anti-Ni) | 8 | 45.8 ± 6.9 | 8.3 ± 3.9 |
| 3202 (oligo-dT) | 8 | 56.4 ± 6.3 | 3.7 ± 2.1 |
| 3064 (anti-myelin) | 6 | 41.8 ± 7.5 | 26.2 ± 7.3 |

[1]Number of mice in each treatment group

Statistical Comparisons:
3064 to 3202, p=0.008
3064 to 3060, p=0.043
3060 to 3202, p=0.505
All statistics by comparing groups using rank order sum test.

Figure 9B:
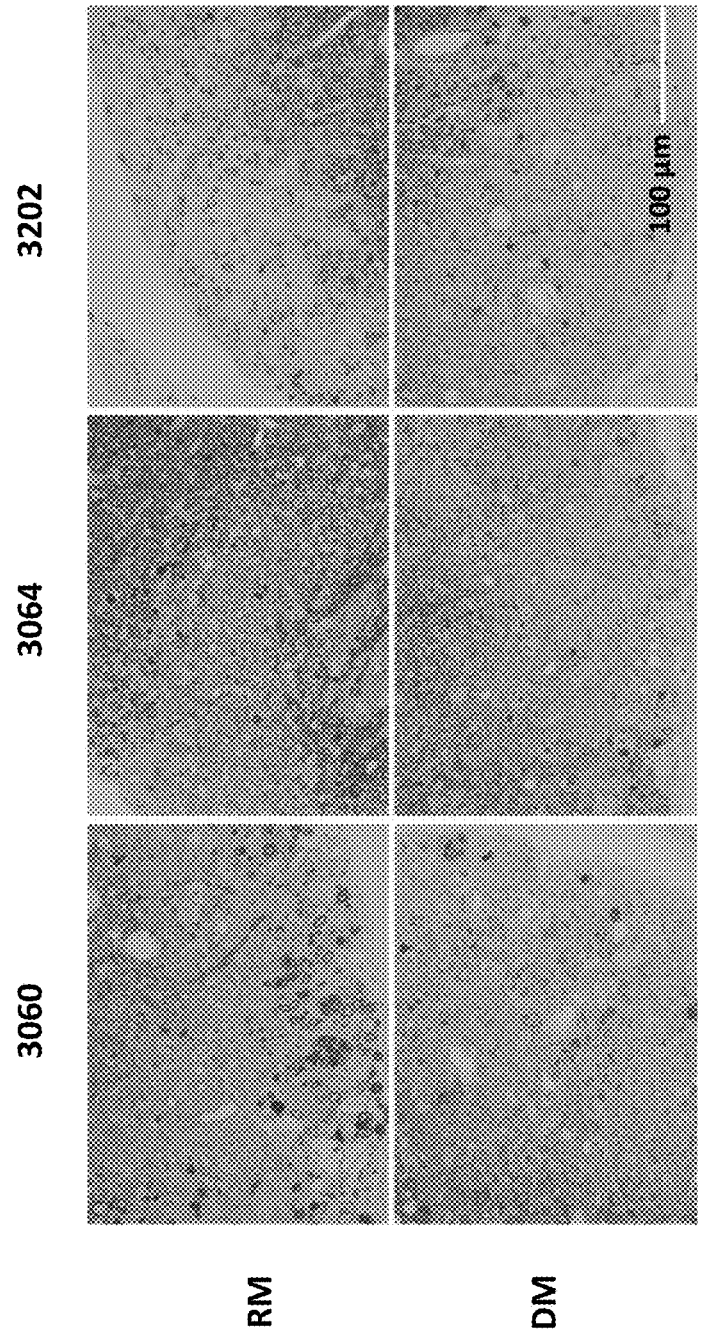
FIG. 9B is a series of light photomicrographs demonstrating examples of TMEV-mediated spinal cord demyelination (lower panels) and remyelination (upper panels) in mice treated with the indicated DNA aptamers. The scale bar in lower right panel is 100 micrometers. After blinded micrograph review of specimens from control and aptamer-treated animals, the percent of spinal cord quadrants showing demyelination or remyelination was determined as reported in Table 2.

Further experiments were conducted to compare the effect of aptamers administered to mice in the presence or absence of biotin and avidin. As above, the Theiler's virus model of MS was used for these experiments. Mice were treated 6 to 9 months after infection—a time point of maximal demyelination and minimal remyelination. All data were collected on coded samples where the only information was the animal number on the slide. Spinal cords from all mice in the study contained areas of chronic demyelination. Infiltrating macrophages were present in several lesions. Remyelination was characterized by densely packed thin myelin sheaths in relation to axon diameter. In mice treated with anti-myelin aptamer 3064, more areas of dense remyelinated axons were found (FIG. 9B). For example, the top middle panel of FIG. 9B shows an area of almost complete remyelination mediated by oligodendrocytes located in the dorsal white matter column of the spinal cord of a mouse treated with anti-myelin aptamer 3064. In mice treated with control aptamers 3060 and 3202, dorsal column spinal cords lesions contained fewer remyelinated axons.

As indicated in Table 2 below, mice that received aptamer 3064 (anti-myelin) with the presumed tetrameric structure showed remyelination in 35% of experimental CNS lesions, compared to 4% and 9% remyelination after treatment with negative control aptamers 3202 ($dT_{40}$) and 3060 (anti-Ni), respectively. Animals that received aptamer 3064 alone (without biotin-avidin) showed remyelination similar to the controls. These statistically significant results suggested that the aptamer must be in the "tetrameric" structure in order to promote remyelination in vivo. Interestingly, animals injected with streptavidin and non-biotinylated aptamers 3064 or 3060 did not show remyelination, suggesting that aptamer 3' modification was important for protection from nuclease attack and/or for streptavidin binding to form multivalent conjugates.

TABLE 2

Remyelination in vivo after treatment with DNA aptamers with and without biotin-avidin

| Treatment | N* | Gray Matter | Inflammation | Demyelination | Remyelination |
|---|---|---|---|---|---|
| 3064 w/biotin-avidin | 10 | 0.0 ± 0.0 | 6.0 ± 3.1 | 41.1 ± 6.4 | 34.9 ± 6.1 |
| 3060 w/biotin-avidin | 7 | 0.0 ± 0.0 | 14.5 ± 6.2 | 38.2 ± 8.7 | 8.8 ± 4.5 |
| 3202 w/biotin-avidin | 8 | 0.0 ± 0.0 | 3.5 ± 1.1 | 51.8 ± 26.4 | 4.2 ± 2.3 |
| 3064 w/o biotin-avidin | 9 | 0.0 ± 0.0 | 13.1 ± 6.6 | 42.0 ± 5.8 | 8.5 ± 3.4 |
| 3060 w/o biotin-avidin | 8 | 0.0 ± 0.0 | 30.5 ± 7.3 | 50 ± 4.6 | 10.3 ± 4.4 |

*N = number of mice

Table indicates lesion status, by animal, after blinded review of neuropathology. Data are expressed as the percent of spinal cord quadrants showing that at least 75% of the lesion was remyelinated (mean±SEM).

Statistical comparisons: $p<0.002$ for remyelination—(ANOVA on Ranks); Dunn's comparison to $dT_{40}$ (control) showed statistical difference ($p<0.05$) against the myelin-reactive 3064 aptamer with biotin/avidin. There was no significant difference in remyelination between antisense (control) and the myelin reactive 3064 aptamer without biotin-avidin.

Further experiments with additional mice confirmed these results. Data from all of the experiments are presented in Table 3A, with statistical results in Table 3B.

TABLE 3A

| Treatment | N* | Gray Matter | Inflammation | Demyelination | Remyelination |
|---|---|---|---|---|---|
| 3064 w biotin-avidin | 15 | 0.0 ± 0.0 | 10.3 ± 3.0 | 39.4 ± 4.4 | 32.3 ± 4.3 |
| 3060 w/biotin-avidin | 7 | 0.0 ±0.0 | 14.5 ± 6.2 | 38.2 ± 8.7 | 8.8 ± 4.5 |
| 3202 w/biotin-avidin | 7 | 0.0 ± 0.0 | 3.5 ± 1.1 | 51.8 ± 26.4 | 4.2 ± 2.3 |
| 3064 w/o biotin-avidin | 9 | 0.0 ± 0.0 | 13.1 ± 6.6 | 42.0 ± 5.8 | 8.5 ± 3.4 |
| 3060 w/o biotin-avidin | 6 | 0.0 ± 0.0 | 30.5 ± 7.3 | 50 ± 4.6 | 10.3 ± 4.4 |
| Streptavidin only (no aptamer) | 15 | 0.0 ± 0.0 | 17.2 ± 3.1 | 47.4 ± 3.4 | 10.7 ± 2.7 |
| No aptamer | 6 | 0.0 ± 0.0 | 20.2 ± 4.5 | 46.2 ± 7.7 | 7.2 ± 2.5 |

*N = number of mice

Data are expressed as the percent of spinal cord quadrants showing pathologic abnormality (mean±SEM).

Statistical comparisons: $p<0.001$ remyelination—(ANOVA on Ranks); Dunn's comparison to $dT_{40}$ (control) showed statistical difference ($p<0.05$) against the myelin-reactive 3064 aptamer with biotin/streptavidin. No significant difference in remyelination was observed between $dT_{40}$ (control) and aptamer 3064 without biotin-streptavidin.

TABLE 3B

| Parameter | Group | Group | Statistics | Value |
|---|---|---|---|---|
| Remyelination | All | ranks | ANOVAs | $p < 0.001$ |
| Demyelination | All | ranks | ANOVAs | $p = 0.391$ |
| Inflammation | All | ranks | ANOVAs | $p = 0.448$ |
| Remyelination | 3064 w/biotin | 3202 w/biotin | T test | $p = 0.038$ |
| Demyelination | 3064 w/biotin | 3202 w/biotin | T test | $p = 0.156$ |
| Remyelination | 3064 w/o biotin | 3064 w/o biotin | T test | $p = 0.002$ |
| Remyelination | 3064 w/o biotin | Streptavidin only | T test | $p < 0.001$ |

The aptamer-induced remyelination described herein was comparable to effects obtained in studies using much larger and more labile human IgM autoantibodies. The present results raised the possibility that the observed remyelination activity of anti-myelin DNA aptamers also may reflect direct interactions with lesions, though this remains to be demonstrated. The abilities of certain natural IgM autoantibodies to stimulate cell signaling and remyelination depend on the multivalent character of the antibody structure (Paz Soldan, supra). It is noteworthy that the formulation of biotinylated DNA aptamers with streptavidin is likely to organize tetravalent complexes by virtue of intermolecular guanosine quartets (see, e.g., FIG. 1C).

The molecular mass of anti-myelin DNA aptamer 3064 is ~13,000. Even fully tetramerized with streptavidin (mass ~52,800), the resulting complex (mass ~104,800) is still about 10-fold smaller than the IgM antibodies previously shown to promote remyelination. In addition, DNA aptamers can be prepared by chemical synthesis, and are less likely than IgM antibodies to be immunogenic. These considerations suggest that DNA aptamer reagents may be useful as a therapeutic for treatment of MS and other demyelinating diseases.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a subject identified as having multiple sclerosis, comprising administering to the subject a pharmaceutical composition comprising a multimeric nucleic acid aptamer in an amount effective to promote remyelination, wherein the nucleic acid aptamer comprises the sequence set forth in SEQ ID NO:17.

2. The method of claim 1, wherein the nucleic acid aptamer is a homotetramer.

3. The method of claim 1, wherein the remyelination is mediated by central nervous system-type myelin producing cells or by peripheral nervous system-type myelin producing cells.

4. The method of claim 1, wherein the nucleic acid aptamer is administered in an amount effective to reduce demyelination or increase remyelination in the central nervous system of the subject.

5. The method of claim 4, wherein the demyelination is reduced by at least 10% as compared to the level of demyelination in the subject prior to administration of the nucleic acid aptamer.

6. A method for treating a subject identified as having multiple sclerosis, comprising administering to the subject a multimeric nucleic acid aptamer in an amount effective to promote remyelination, wherein the nucleic acid aptamer comprises the sequence set forth in SEQ ID NO:17.

7. The method of claim 6, wherein the nucleic acid aptamer is a homotetramer.

8. The method of claim 6, wherein the remyelination is mediated by central nervous system-type myelin producing cells or by peripheral nervous system-type myelin producing cells.

9. The method of claim 6, wherein the nucleic acid aptamer is administered in an amount effective to reduce demyelination or increase remyelination in the central nervous system of the subject.

10. The method of claim 9, wherein the demyelination is reduced by at least 10% as compared to the level of demyelination in the subject prior to administration of the aptamer.

* * * * *

SEQUENCE LISTING

<160> NUMBER OF SEQ ID NOS: 21

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
ataccagctt attcaatt                                                    18

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
aaaaaaaaaa aaaaaaaaaa agattgcact tactatct                              38

<210> SEQ ID NO 3
<211> LENGTH: 96
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 50, 71, 78
<223> OTHER INFORMATION: n = any nucleotide

<400> SEQUENCE: 3
ataccagctt attcaattgg gtcggcgggt ggggtgggag gtggtcttgn ctctgggttt      60
tgttgtgaac nacgcgtnag atagtaagtg caatct                               96

<210> SEQ ID NO 4
<211> LENGTH: 96
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 35, 78
<223> OTHER INFORMATION: n = n = any nucleotide

<400> SEQUENCE: 4
ataccagctt attcaattgg gtcggcgggt ggggngggag gtggtcttgt ctctgggttt      60
tgttgtgaac cacgcgtnag atagtaagtg caatct                               96

<210> SEQ ID NO 5
<211> LENGTH: 96
<212> TYPE: DNA
<213> ORGANISM: Artificial Sequence
<220> FEATURE:
<223> OTHER INFORMATION: synthetic oligonucleotide

<400> SEQUENCE: 5
ataccagctt attcaattgg gtcggcgggt ggggtgggag gtggtcttgt ctctgggttt      60
tgttgtgaac cacacgtaag atagtaagtg caatct                               96

<210> SEQ ID NO 6
<211> LENGTH: 99

```
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 39, 59, 81
<223> OTHER INFORMATION: n = any nucleotide

<400> SEQUENCE: 6
ataccagctt attcaattgg gggggagggg ctagcccgng ggaaggaggc taggctggna    60
gtgtggagac cgtgggtgct nagatagtaa gtgcaatct                          99

<210> SEQ ID NO 7
<211> LENGTH: 96
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 37, 47
<223> OTHER INFORMATION: n = any nucleotide

<400> SEQUENCE: 7
ataccagctt attcaattgt gggggggag gggcggngac ggagggngca tcatcaacca     60
aacctggccg gagagcgcac atagtaagtg caatct                             96

<210> SEQ ID NO 8
<211> LENGTH: 96
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 76
<223> OTHER INFORMATION: n = any nucleotide

<400> SEQUENCE: 8
ataccagctt attcaattga caggcggggc ggggtggagg gggcaggtgg tcggtccaat    60
aaagcgtcga tggcgnccag atagtaagtg caatct                             96

<210> SEQ ID NO 9
<211> LENGTH: 97
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 36, 66, 71
<223> OTHER INFORMATION: n = any nucleotide

<400> SEQUENCE: 9
ataccagctt attcaattga tatgaggggt gggtgnccgg gcgaacatgg gggtggaggt    60
cagtcngtgg ntaaaaccca gatagtaagt gcaatct                            97

<210> SEQ ID NO 10
<211> LENGTH: 96
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 37, 38
```

<223> OTHER INFORMATION: n = any nucleotide

<400> SEQUENCE: 10
ataccagctt attcaattcc ggttgggagg gataatnngg ggaggcggtg gctatagggt    60
cgtccaaaca gctgcccaag atagtaagtg caatct    96

<210> SEQ ID NO 11
<211> LENGTH: 97
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 32, 79
<223> OTHER INFORMATION: n = any nucleotide

<400> SEQUENCE: 11
ataccagctt attcaattac aacacagtct anccgacaaa ccatctatct cgatctatgc    60
atgaacacca cttcccgcna gatagtaagt gcaatct    97

<210> SEQ ID NO 12
<211> LENGTH: 95
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 43, 60, 77
<223> OTHER INFORMATION: n = any nucleotide

<400> SEQUENCE: 12
ataccagctt attcaattaa cgagggggt gggtggggcg ggntccgagg acatgctagn    60
tggttcaggc tggttanaga tagtaagtgc aatct    95

<210> SEQ ID NO 13
<211> LENGTH: 97
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 21, 37
<223> OTHER INFORMATION: n = any nucleotide

<400> SEQUENCE: 13
ataccagctt attcaatttc ngggcgaggg tgggggnaag aaagctgggg gggtaggcag    60
ggtctgaatc gtgttcggca gatagtaagt gcaatct    97

<210> SEQ ID NO 14
<211> LENGTH: 95
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 24, 27, 57
<223> OTHER INFORMATION: n = any nucleotide

<400> SEQUENCE: 14
ataccagctt attcaattat gggnaanagg gttggccggg ggagagagga ggtcggngat    60
ggtatgcgcc gggttctaga tagtaagtgc aatct    95

<210> SEQ ID NO 15
<211> LENGTH: 94
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 23, 38, 40
<223> OTHER INFORMATION: n = any nucleotide

<400> SEQUENCE: 15
ataccagctt attcaattgg aanggttgga gggctggncn atgtagagac cggggagga      60 ggcaacatac gtgccgagat agtaagtgca atct                                94

<210> SEQ ID NO 16
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 16
ataccagctt attcaattgg gtcggcgggt ggggtgggag                           40

<210> SEQ ID NO 17
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 17
gggtcggcgg gtggggtggg aggtggtctt gtctctgggt                           40

<210> SEQ ID NO 18
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 18
ataccagctt attcaattgg gtcggcgggt ggggtgggag                           40

<210> SEQ ID NO 19
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 19
gttttgttgt gaaccacacg taagatagta agtgcaatct                           40

<210> SEQ ID NO 20
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 20
aaagaacaaa aaggataaag ggggagacgg ggggaacatg ggg                       43

```
<210> SEQ ID NO 21
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 21
tttttttttt tttttttttt tttttttttt tttttttttt                              40
```